United States Patent
Patel et al.

(10) Patent No.: US 7,427,414 B2
(45) Date of Patent: Sep. 23, 2008

(54) MODIFIED RELEASE ORAL DOSAGE FORM USING CO-POLYMER OF POLYVINYL ACETATE

(75) Inventors: Shashank Bababhai Patel, Ahmedabda (IN); Kamala Sultansingh Yadav, Gandhinagar (IN); Jayant Kumar Mandal, Jamshedpur (IN); Kirti Bansidhar Maheshwari, Ahmedabad (IN)

(73) Assignee: Astron Research Limited, Ahmedabad (IN)

( * ) Notice: Subject to any disclaimer, the term of this patent is extended or adjusted under 35 U.S.C. 154(b) by 138 days.

(21) Appl. No.: 11/623,560

(22) Filed: Jan. 16, 2007

(65) Prior Publication Data

US 2007/0166375 A1 Jul. 19, 2007

(30) Foreign Application Priority Data

Jan. 18, 2006 (IN) .......................... 83/MUM/2006

(51) Int. Cl.
*A61K 9/14* (2006.01)
*A61K 31/44* (2006.01)
*A61K 31/135* (2006.01)
*A01N 37/02* (2006.01)
*A01N 33/02* (2006.01)

(52) U.S. Cl. ....................... 424/489; 514/338; 514/548; 514/649; 514/651

(58) Field of Classification Search ................. 424/400, 424/451, 458, 464, 469, 489; 514/571, 960, 514/962, 963, 964, 548, 338, 649, 651
See application file for complete search history.

(56) References Cited

U.S. PATENT DOCUMENTS

| | | | |
|---|---|---|---|
| 4,824,678 A | 4/1989 | Lindahl et al. | |
| 6,306,436 B1 | 10/2001 | Chungi et al. | |
| 6,368,625 B1 | 4/2002 | Siebert et al. | |
| 7,037,525 B2 * | 5/2006 | Schlutermann | 424/474 |
| 2003/0190354 A1 | 10/2003 | Sela | |
| 2004/0096501 A1 | 5/2004 | Vaya et al. | |
| 2005/0112198 A1 * | 5/2005 | Challapalli et al. | 424/464 |
| 2005/0118264 A1 | 6/2005 | Sela | |
| 2005/0203186 A1 * | 9/2005 | Kraass | 514/571 |
| 2006/0153916 A1 | 7/2006 | Vaya et al. | |
| 2006/0182797 A1 | 8/2006 | Karavas et al. | |
| 2006/0204587 A1 | 9/2006 | Kolter et al. | |

FOREIGN PATENT DOCUMENTS

WO 2005/112901 12/2005

* cited by examiner

*Primary Examiner*—Johann R. Richter
*Assistant Examiner*—Konata M. George
(74) *Attorney, Agent, or Firm*—Hamre, Schumann, Mueller & Larson, P.C.

(57) ABSTRACT

Once a day modified release oral dosage form comprising of granules or pellets which are either compressed into tablet or filled inside the capsule, wherein the pellet has a core of active ingredient coated on non pareil seeds with a rate controlling functional coating of co-polymer of polyvinyl acetate optionally with an intermediate separating coating between the core and the functional coating layer.

21 Claims, No Drawings

MODIFIED RELEASE ORAL DOSAGE FORM USING CO-POLYMER OF POLYVINYL ACETATE

FIELD OF THE INVENTION

The present invention relates to the use of co-polymer of polyvinyl acetate as the release-controlling agent for once a day modified release oral pharmaceutical dosage form. This dosage form comprises of granules or pellets which is either compressed to form tablet or filled inside the capsule with suitable pharmaceutically acceptable excipients.

BACKGROUND

Immediate release dosage forms of pharmaceutically active ingredient results rapid dissolution and rapid rise in plasma drug concentration within a short period of dosage form administration. Subsequently, due to metabolism and elimination, the plasma concentrations fall below the therapeutic level within period of 8-12 hours, thus requiring additional dosing, which may cause unpleasant side effects.

In order to avoid such high fluctuations in plasma concentration, the release of pharmaceutically active ingredient should be controlled in the gastrointestinal tract, so as to have a prolonged effect of drug even after a dose of once or twice a day, more preferably once a day.

Immediate release dosage forms of pharmaceutically active ingredients such as Venlafaxine hydrochloride, Bupropion hydrochloride, Pravastatin, etc results in a high plasma concentration, which causes unpleasant side effects, such as nausea or vomiting in a considerable part of the patients. In order to avoid such high plasma concentration the release of drugs should be controlled throughout the gastrointestinal tract

OBJECTS OF THE INVENTION

First object of the invention is to provide an oral controlled release pharmaceutical dosage form of pharmaceutically active ingredients.

Another object of the invention is to prepare an oral dosage form preferably capsule or tablet of a pharmaceutically active ingredients using co-polymer of polyvinyl acetate as the release controlling agent.

Still another object of invention is to provide orally administrable modified release pharmaceutical dosage form of different actives such as Venlafaxine hydrochloride, Bupropion hydrochloride, Pravastatin, Lansoprazole, etc.

Still another object of invention is to provide once or twice a day more preferably once a day oral modified release pharmaceutical dosage form of pharmaceutically active ingredients.

One more object of the invention is to provide a process for the preparation of oral modified release pharmaceutical oral dosage form of pharmaceutically active ingredient and pharmaceutically acceptable salts thereof.

This present invention further aims to develop a pharmaceutical formulation for oral use providing release of an active ingredient through out the gastro intestinal tract or can be modified to target a segment of the gastrointestinal tract.

SUMMARY OF THE INVENTION

The present invention relates to the use of co-polymer of polyvinyl acetate for the preparation of modified release pharmaceutical oral dosage form of pharmaceutically active ingredient. This dosage form is in the form of pellets or granules which are either compressed to form tablet or filled inside capsule. The controlled release of pharmaceutically active ingredient through out the gastrointestinal tract is achieved by the process of coating the co-polymer of polyvinyl acetate onto the core of drug like drug loaded non-pareil seeds or drug containing pellets or alternatively by including it in the core tablets to form a matrix which controls the drug release.

DETAILED DESCRIPTION OF THE INVENTION

The present invention provides an oral modified release pharmaceutical dosage form of pharmaceutically active ingredients using co-polymer of polyvinyl acetate as the release controlling excipient.

The dosage form can be in the form of granules or pellets which is either compressed to form tablet or filled inside a capsule or alternatively matrix tablets used once or twice a day, more preferably once a day.

The oral dosage form provides release of the active ingredient through out the gastro intestinal tract or can be modified to target a segment of the gastrointestinal tract.

To have controlled release of drugs such as Venlafaxine hydrochloride, Bupropion, Lansoprazole, Pravastatin etc. the dosage form is prepared using co-polymer of polyvinyl acetate. The polymer may be present in the core tablets to form a matrix dosage form, which will control the release of the drug from it. Alternatively, it may also be used in the coating solution to provide a release controlling layer from which the drug will be released gradually. In addition, the polymer may also be coated onto drug loaded non-pareil seeds or drug containing pellets to provide a controlled release barrier film.

The present invention provides a modified release pharmaceutical oral dosage form of a pharmaceutically active ingredient. This dosage form comprises diluents 15-25%, active ingredient 5-50%, polymer 0.5-15%, glidant 0.1-10%, opacifier/color 0.1-10%, retardant 5-25%, plasticizer 0.5-10% and solvent as per the requirement.

These ingredients can be used in the amount as per the requirement in different stage of the process for preparation of the dosage form.

Modified release in the present invention means release of active ingredient from the dosage form through out the gastrointestinal tract for prolonged period. The dissolution of the active ingredient in 2 hr—not more than 50%, in 6 hr—40-70%, in 12 hr—50-90% and in 24 hr—not less than 80%

The diluents used may be those commonly used in tablets dosage form such as lactose, starch, microcrystalline cellulose, dicalcium phosphate, or combinations thereof.

Alternatively non-pareil seeds can be cellulose base or sugar base.

The pharmaceutically active ingredient can be selected from the group comprising of but not limited to class of phenethyl amines such as Bupropion & its salts and analogues, serotonin noradrenaline reuptake inhibitor like venlafaxine and its analogues, Benzimidazole class of proton pump inhibitors such as lansoprazole and its salts and analogues, HMG-CoA reductase inhibitors such as Pravastatin and its salts and analogues, etc.

Polymers can be pharmaceutically acceptable polymers or waxes selected from the group comprising of but not limited to cellulose and cellulose derivatives such as hydroxypropyl methyl cellulose, hydroxypropyl cellulose, hydroxyethyl cellulose, microcrystalline cellulose, carboxymethylcellulose, sodium carboxymethylcellulose, calcium carboxymethylcellulose, methylcellulose and ethylcellulose; alginates such as sodium alginate, polyvinylpyrrolidones, polyethylenoxides and polyacrylic/methacrylic acids including their copolymers and crosslinked polymers thereof, i.e. carbopol, Eudragit, polycarbophil and chitosan polymers, waxes include white beeswax, microcrystalline wax, carnauba wax, hydrogenated castor oil, glyceryl behenate, glycerylpalmito stearate, saturated polyglycolyzed glycerate and the like.

Rate controlling retardants can be copolymer of polyvinyl acetate and the like.

Film former comprises of sodium alginate and the likes.

Glidants or anti-sticking agents can be selected from the group comprising of but not limited to talc, colloidal silicon dioxide, stearic acid and stearates such as magnesium stearate, calcium stearate, glycerly monostearate and the like.

Opacifier can be titanium dioxide and the like

Plasticizers can be selected from the group comprising of but not limited to acetyltributyl citrate, triacetin, acetyltriethyl citrate, dioctylphthalate, dibutylphthalate, triethyl citrate, tributylcitrate, polyethylene glycol, propylene glycol and the like.

Solvents can be water, isopropanol, acetone, ethanol and the like.

One of the methods for preparing the dosage form of the present invention could be by fluidized bed coating technology, which comprises following steps:

1) Load the drug on non-pareil seeds (NPS) in the form of a solution containing the pharmaceutically active ingredient along with suitable excipients such as polymer, glidant, opacifier, colorant, etc by fluid bed coating technique OR alternatively drug containing pellets may be prepared by the process of extrusion/spheronization wherein the active ingredient is mixed with suitable excipients such as but not limited to starch, microcrystalline cellulose, dicalcium phosphates, glucose, lactose, Mannitol, etc.
2) Seal coating the drug loaded pellets using solution containing excipients such as film former, polymer, glidant, opacifier, colorant, etc. by fluid bed coating technique.
3) Functional coat the seal coated pellets using solution containing excipients such as retardant, plasticizer, colorant, opacifier, glidant, etc. by fluid bed coating technique.

The pellets thus prepared can be filled in capsules or compressed into tablets after mixing with other suitable excipients. For capsules, the shell used can be of gelatin, hydroxy propyl methylcellulose and the like.

Alternatively the controlled release dosage form can also be prepared by the process of dry granulation method or direct compression method or wet granulation method or melt granulation method wherein the release controlling agent may be incorporated with the active pharmaceutical ingredient and other suitable commonly used excipients so as to obtain granules, which may then be compressed into tablets or filled into capsules.

An alternate process would be to prepare the pellets as stated earlier, mix them with suitable excipients and compress them into tablets Throughout this specification and the appended claims it is to be understood that the words "comprise" and include" and variations such as "comprises", "comprising", "includes", "including" are to be interpreted inclusively, unless the context requires otherwise. That is, the use of these words may imply the inclusion of an element or elements not specifically recited.

EXAMPLE 1

The present invention has been described by way of example only, and it is to be recognized that modifications thereto which fall within the scope and spirit of the appended claims, and which would be obvious to a skilled person based upon the disclosure herein, are also considered to be included within the invention.

The above said invention can be illustrated by but not limited to following examples.

37.5 mg Venlafaxine capsule comprises non peril seeds 17.26%, Venlafaxine HCl 44.24%, sodium alginate 17.91%, talc 5.6%, Kollicaot SR30 D (copolymer of polyvinyl acetate), 12.03%, and purified water in required quantity. These ingredients are used in different stage and in different proportion in the process of preparation of the said capsule.

| Formulation of Venlafaxine HCl (37.5 mg Venlafexine) Capsules | | |
|---|---|---|
| Sr. No. | Ingredients | mg/cap |
| 1 | Non Pareil Seeds | 16.546 |
| | Drug Coating | |
| 2 | Venlafaxine HCl | 42.400 |
| 3 | Sodium Alginate | 11.660 |
| 4 | Talc | 1.930 |
| 5 | Titanium Dioxide | 1.250 |
| 6. | Purified Water | Q.S.* |
| | Sub Total | 73.786 |
| | Seal Coating | |
| 7. | Sodium Alginate | 5.510 |
| 8. | Talc | 0.892 |
| 9. | Titanium Dioxide | 0.392 |
| 10. | Purified Water | Q.S.* |
| | Sub Total | 80.580 |
| | Functional Coating | |
| 11. | Kollicoat SR30D | 11.535 |
| 12. | Propylene Glycol | 1.154 |
| 12. | Talc | 2.551 |
| 13. | Purified Water | Q.S.* |
| | Total | 95.82 |

*Does not remain in formulation.

Process:
1) Load the drug on NPS using solution containing Venlafaxine HCl, sodium alginate, talc & titanium dioxide by fluid bed coating technique.
2) Seal coating the drug coated pellets using solution containing sodium alginate, talc & titanium dioxide by fluid bed coating technique
3) Functional coat the seal coated pellets using solution containing Kollicoat SR 30D, propylene glycol & talc by fluid bed coating technique

EXAMPLE 2

37.5 mg Venlafaxine capsule comprises non peril seeds 26.67%, Venlafaxine HCl 35.33%, sodium alginate 13.83%, Talc 5.32%, Kollicoat SR30D (copolymer of polyvinyl acetate) 14.83%, propylene glycol 1.50% and purified water in required quantity. These ingredients are used in different stage and in different proportion in the process of preparation of the said capsule.

| Formulation of Venlafaxine HCl (37.5 mg Venlafexine) Capsules | | |
|---|---|---|
| Sr. No. | Ingredients | mg/cap |
| 1 | Non Pareil Seeds | 32.00 |
| | Drug Coating | |
| 2 | Venlafaxine HCl | 42.4 |
| 3 | Sodium Alginate | 10.60 |
| 4 | Talc | 2.0 |
| 5 | Titanium Dioxide | 2.0 |
| 6. | Purified Water | Q.S.* |
| | Sub Total | 89.00 |
| | Seal Coating | |
| 7. | Sodium Alginate | 6.0 |
| 8. | Talc | 1.0 |
| 9. | Titanium Dioxide | 1.0 |
| 10. | Purified Water | Q.S.* |
| | Sub Total | 97.00 |
| | Functional Coating | |
| 11. | Kollicoat SR30D | 17.80 |
| 12. | Propylene Glycol | 1.8 |
| 13. | Talc | 3.40 |
| 14. | Purified Water | Q.S.* |
| | Total | 120.00 |

*Does not remain in formulation.

Process:
1) Load the drug on NPS using solution containing Venlafaxine HCl, sodium alginate, talc & titanium dioxide by fluid bed coating technique.
2) Seal coating the drug coated pellets using solution containing sodium alginate, talc & titanium dioxide by fluid bed coating technique
3) Functional coat the seal coated pellets using solution containing Kollicoat SR30D, propylene glycol & talc by fluid bed coating technique

EXAMPLE 3

| Formulation of Bupropion hydrochloride tablets 150 mg | | |
|---|---|---|
| Sr. No. | Ingredients | mg/tablet |
| 1. | Bupropion Hydrochloride | 150 |
| 2. | Microcrystalline cellulose | 40 |
| 3. | Maize starch | 29.5 |
| 4. | Co-polymer of polyvinyl acetate | 60.0 |
| 5. | Ethyl cellulose | 120.0 |
| 6. | Hydrochloric Acid | 2.5 |
| 7. | Purified Water | QS |
| 8. | Mg. Stearate | 4.0 |
| 9. | Opadry | 10.0 |

Process: Granulate Bupropion hydrochloride, microcrystalline cellulose, maize starch, co-polymer of polyvinyl acetate, and ethyl cellulose using water containing hydrochloric acid, dry the granules and lubricate suitably.

These granules can then be compressed into tablets using suitable punches and coated using Opadry.

EXAMPLE 4

| Formulation of Pravastatin tablets 10 mg | | |
|---|---|---|
| Sr. No. | Ingredients | mg/tablet |
| 1 | Non Pareil Seeds | 10.3 |
| 2 | Pravastatin sodium | 10.3 |
| 3 | HPMC | 1.3 |
| 4 | Talc | 5.7 |
| 5. | Purified Water | QS |
| | Functional Coating | |
| 6. | Kollicoat SR30D | 8.9 |
| 7. | Propylene Glycol | 0.5 |
| 8. | HPMC | 5.0 |
| 9. | Talc | 0.3 |
| 10. | Purified Water | QS |
| | Lubrication | |
| 11. | Microcrystalline cellulose | 46.45 |
| 12. | Crosscarmellose sodium | 10.0 |
| 13. | Magnesium Stearate | 1.25 |
| | Total | 100.00 |

Process:
1) Load the drug on NPS using solution containing pravastatin sodium, HPMC and talc.
2) Functional coat the drug coated core using solution of Kollicoat SR30D, propylene glycol, HPMC & talc by fluid bed coating technique.
3) Lubricate the pellets with microcrystalline cellulose, cross carmellose sodium and magnesium stearate.
4) Compress the pellets into tablet.

We claim:
1. A once a day modified release oral dosage form comprising:
   a core coated with an active pharmaceutical ingredient;
   a copolymer of polyvinyl acetate as a release controlling agent; and
   a pharmaceutically acceptable excipient,
   wherein the active pharmaceutical ingredient is highly water soluble, and the core comprises a nonpareil seed.
2. The dosage form as claimed in claim 1, wherein the active ingredient can be serotonin noradrenaline reuptake inhibitor, phenyl ethyl amines, benzimidazole class of proton pump inhibitor, or HMG-CoA reductase inhibitor.
3. The dosage form as claimed in claim 2, wherein the serotonin noradrenaline reuptake inhibitor is venlafaxine or its pharmaceutically acceptable salt, phenylethyl amine is bupropion or its pharmaceutically acceptable salt, benzimidazole class of proton pump inhibitor is lansoprazole or its pharmaceutically acceptable salt and HMG-CoA reductase inhibitor is pravastatin or its pharmaceutically acceptable salt.
4. The dosage form as claimed in claim 1, wherein pellets that are prepared are compressed into tablets or filled inside capsules.
5. The dosage form as claimed in claim 4, wherein the pellets comprise the drug loaded core and a release controlling functional coating optionally with an intermediate barrier/separating coating between the drug loaded core and the functional coating.
6. The dosage form as claimed in claim 5, wherein the functional coating comprises the copolymer of polyvinyl acetate, a plasticizer, and a glidant.

7. The dosage form as claimed in claim 5, wherein the intermediate barrier/separating coating comprises a film former including sodium alginate, glidant and opacifier.

8. A once a day modified release oral dosage form of bupropion or its pharmaceutically acceptable salt, wherein the dosage form is a tablet comprising bupropion hydrochloride in an amount of 25-50% by weight of the dosage form, co-polymer of polyvinyl acetate in an amount of 5-25% by weight of the dosage form, and other pharmaceutically acceptable excipients.

9. A once a day modified release oral dosage form of venlafaxine or its pharmaceutically acceptable salt, comprising a non pareil seed provided as a core, wherein venlafaxine hydrochloride and sodium alginate are coated on the core, and the drug coated core is further coated with an intermediate barrier coating comprising sodium alginate, glidant, opacifier and other pharmaceutically acceptable excipient and a final release controlling functional coating comprising a copolymer of polyvinyl acetate.

10. The dosage form as claimed in claim 9, wherein pellets are filled inside capsules or compressed to form tablets.

11. The dosage form as claimed in claim 9, wherein the drug coated core comprises venlafaxine hydrochloride in an amount of 25-50% by weight of the dosage form and sodium alginate in an amount of 5-15% by weight of the dosage form, the intermediate barrier coating comprises sodium alginate in an amount of 1-10% by weight of the dosage form and the functional coating comprises the copolymer of polyvinyl acetate in an amount of 5-25% by weight of the dosage form.

12. The dosage form as claimed in claim 9, wherein the copolymer of polyvinyl acetate is Kollicoat SR 30 D.

13. The dosage form as claimed in claim 8, wherein granules are prepared by dry granulation method or wet granulation method or melt granulation method.

14. The dosage form as claimed in claim 1, wherein the dosage form is a tablet prepared by compressing pellets and suitable excipients, wherein the pellets comprises the core and the core is coated with pravastatin sodium in an amount of 5-50% by weight of the dosage form, hydroxyl propyl methyl cellulose in an amount of 0.5-10% by weight of the dosage form and the copolymer of polyvinyl acetate in an amount of 5-25% by weight of the dosage form.

15. The dosage form as claimed in claim 1, having a dissolution profile as below:

| Time   | % Release |
|--------|-----------|
| 2 hrs  | NMT 50%   |
| 6 hrs  | 40-70%    |
| 12 hrs | 50-90%    |
| 24 hrs | NLT 80%.  |

16. The dosage form as claimed in claim 9, having a dissolution profile as below:

| Time   | % Release |
|--------|-----------|
| 2 hrs  | NMT 50%   |
| 6 hrs  | 40-70%    |
| 12 hrs | 50-90%    |
| 24 hrs | NLT 80%.  |

17. The dosage form as claimed in claim 8 having a dissolution profile as below:

| Time   | % Release |
|--------|-----------|
| 2 hrs  | NMT 50%   |
| 6 hrs  | 40-70%    |
| 12 hrs | 50-90%    |
| 24 hrs | NLT 80%.  |

18. The dosage form as claimed in claim 14 having a dissolution profile as below:

| Time   | % Release |
|--------|-----------|
| 2 hrs  | NMT 50%   |
| 6 hrs  | 40-70%    |
| 12 hrs | 50-90%    |
| 24 hrs | NLT 80%.  |

19. The dosage form as claimed in claim 13, wherein the granules are compressed into the tablet.

20. The dosage form as claimed in claim 8, wherein the copolymer of polyvinyl acetate is Kollicoat SR 30 D.

21. The dosage form as claimed in claim 14, wherein the copolymer of polyvinyl acetate is Kollicoat SR 30 D.

* * * * *